(12) United States Patent
Lovitt et al.

(10) Patent No.: US 7,534,206 B1
(45) Date of Patent: May 19, 2009

(54) NAVIGATION-ASSISTED FITNESS AND DIETING DEVICE

(75) Inventors: John H. Lovitt, Spring Hill, KS (US); Claudette D. Fisher, Olathe, KS (US)

(73) Assignee: Garmin Ltd. (KY)

( * ) Notice: Subject to any disclaimer, the term of this patent is extended or adjusted under 35 U.S.C. 154(b) by 692 days.

(21) Appl. No.: 11/230,062

(22) Filed: Sep. 19, 2005

(51) Int. Cl.
*A61B 5/00* (2006.01)
*G01B 21/00* (2006.01)

(52) U.S. Cl. .............................. 600/300; 600/481; 482/8
(58) Field of Classification Search ........................ None
See application file for complete search history.

(56) References Cited

U.S. PATENT DOCUMENTS

| | | | |
|---|---|---|---|
| 4,633,216 A | 12/1986 | Tsuyama | 340/432 |
| 4,636,769 A | 1/1987 | Tsuyama | 340/432 |
| 4,642,606 A | 2/1987 | Tsuyama | 340/432 |
| 4,862,395 A | 8/1989 | Fey et al. | 364/561 |
| 4,887,249 A | 12/1989 | Thinesen | 368/10 |
| 5,236,759 A | 8/1993 | Sakurai | 428/76 |
| 5,335,188 A | 8/1994 | Brisson | 702/163 |
| 5,552,989 A | 9/1996 | Bertrand | 701/200 |
| 5,583,776 A | 12/1996 | Levi et al. | 701/217 |
| 5,592,401 A | 1/1997 | Kramer | 702/153 |
| 5,644,511 A | 7/1997 | McWhorter | 702/148 |
| 5,904,442 A | 5/1999 | Takeda | 403/392 |
| 5,941,837 A | 8/1999 | Amano et al. | 600/595 |
| 6,002,982 A | 12/1999 | Fry | 701/213 |
| 6,011,491 A | 1/2000 | Goetzl | 340/870.3 |
| 6,013,007 A * | 1/2000 | Root et al. | 482/8 |
| 6,024,655 A | 2/2000 | Coffee | 473/407 |
| 6,032,108 A | 2/2000 | Seiple et al. | 702/97 |
| 6,067,046 A | 5/2000 | Nichols | 342/357.14 |
| 6,069,788 A | 5/2000 | Masui | 361/683 |
| 6,122,960 A | 9/2000 | Hutchings et al. | 73/493 |
| 6,132,391 A | 10/2000 | Onari et al. | 600/595 |
| 6,134,508 A | 10/2000 | Brandt | 702/142 |
| 6,148,262 A | 11/2000 | Fry | 701/213 |
| 6,182,010 B1 | 1/2001 | Berstis | 701/211 |
| 6,204,752 B1 | 3/2001 | Kishimoto | 340/432 |

(Continued)

OTHER PUBLICATIONS

Trimble News Release, dated Jul. 26, 1996 entitled *Trimble Takes to the Road with Race Across America*, 1 page.

(Continued)

*Primary Examiner*—Robert L Nasser
(74) *Attorney, Agent, or Firm*—Samuel M. Korte

(57) ABSTRACT

A navigation-assisted fitness device broadly comprising a location determining component, a fitness monitoring component and a display. The location determining component determines location data for a user of the device as the user exercises. The fitness monitoring component is coupled with the location determining component and calculates fitness information for the user as the user exercises. The display displays the fitness information and other information and data.

The fitness information may include an indication of the intensity level of the user's exercise, the total amount of calories burned by the user during the exercise, the amount of fat calories burned, and the amount of carbohydrate calories burned. The device calculates the ratio of fat calories burned versus carbohydrate calories burned based on the intensity level. As the user increases or decreases the intensity level of an exercise, the device recalculates and displays the ratio or percentage of total calories burned from fat reserves and from carbohydrate reserves.

13 Claims, 8 Drawing Sheets

U.S. PATENT DOCUMENTS

| | | | |
|---|---|---|---|
| 6,305,221 B1 | 10/2001 | Hutchings | 73/488 |
| 6,328,268 B1 | 12/2001 | Irie | 248/230.1 |
| 6,446,005 B1 | 9/2002 | Bingeman et al. | 701/215 |
| 6,446,922 B2 | 9/2002 | Irie | 248/230.1 |
| 6,449,583 B1 | 9/2002 | Sakumoto et al. | 702/179 |
| 6,463,385 B1 | 10/2002 | Fry | 701/213 |
| 6,498,994 B2 | 12/2002 | Vock et al. | 702/44 |
| 6,546,336 B1 | 4/2003 | Matsuoka et al. | 701/213 |
| 6,549,845 B2 | 4/2003 | Eakle, Jr. et al. | 701/207 |
| 6,549,915 B2 | 4/2003 | Abbott, III et al. | 707/104.1 |
| 6,557,437 B2 | 5/2003 | Masui et al. | 74/551.8 |
| 6,570,532 B2 | 5/2003 | Mise et al. | 342/357.1 |
| 6,571,200 B1 | 5/2003 | Mault | 702/182 |
| 6,582,342 B2 | 6/2003 | Kaufman | 482/8 |
| 6,592,502 B1 * | 7/2003 | Phillips | 482/143 |
| 6,594,617 B2 | 7/2003 | Scherzinger | 702/160 |
| 6,625,523 B2 | 9/2003 | Campagnolo et al. | 701/1 |
| 6,685,634 B1 | 2/2004 | Fry | 600/300 |
| 6,724,299 B2 | 4/2004 | Takeda et al. | 340/432 |
| 6,736,759 B1 * | 5/2004 | Stubbs et al. | 482/8 |
| 2001/0027359 A1 | 10/2001 | Campagnolo | 701/1 |
| 2003/0028116 A1 * | 2/2003 | Bimbaum | 600/500 |
| 2003/0160686 A1 | 8/2003 | Uno | 340/432 |
| 2003/0223905 A1 * | 12/2003 | Moerman | 422/56 |
| 2004/0046692 A1 | 3/2004 | Robson et al. | 342/357.06 |
| 2004/0093126 A1 | 5/2004 | Campagnolo et al. | 701/1 |
| 2004/0095362 A1 | 5/2004 | Koumoto | 345/636 |
| 2004/0102931 A1 * | 5/2004 | Ellis et al. | 702/188 |
| 2004/0117214 A1 * | 6/2004 | Shea | 705/2 |
| 2004/0220712 A1 | 11/2004 | Takeda et al. | 701/35 |

OTHER PUBLICATIONS

News from http://lpc1.clpccd.cc.ca.us/lpc/express/Newshome/11-14/GradSpkr.htm entitled *Commencement speaker shares unique vision*, 3 pages.

The Official Publication of the Hang Gliding and Paragliding Association of Canada, vol. 10, Issue 6, Dec. 1996, p. 29.

Garmin GPS 45 and GPS 40 Frequently Asked Question, Oct. 10, 1995, 6 pages.

TRAX publication from http://caribou.c.trincoll.edu/-lkleinbe/trax/manual.txt, taken from web site Sep. 21, 2001, 3 pages.

Physiology of Exercise; Exercise and Fat Metabolism: Is Low-Intensity Exercise Best for Burning Fat?; pp. 58, 60, 61; 2001.

* cited by examiner

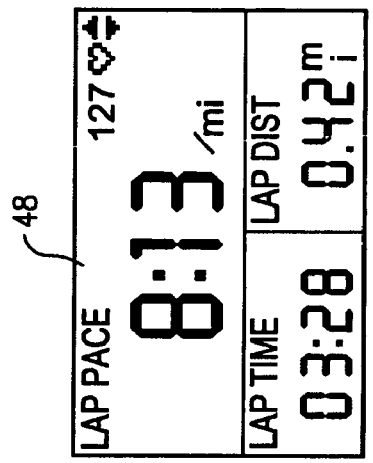
Fig. 6. LAP PAGE
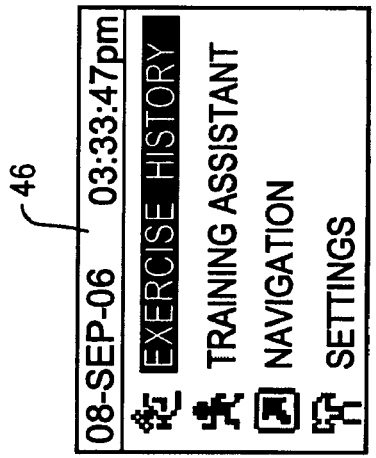
Fig. 5. MENU MODE
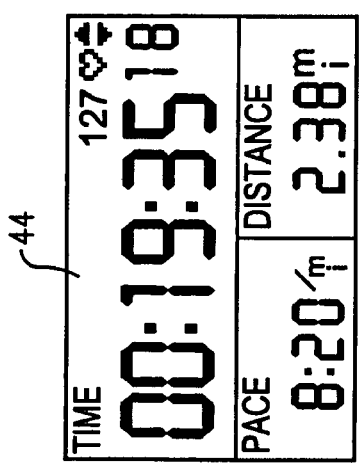
Fig. 4. TIMER MODE
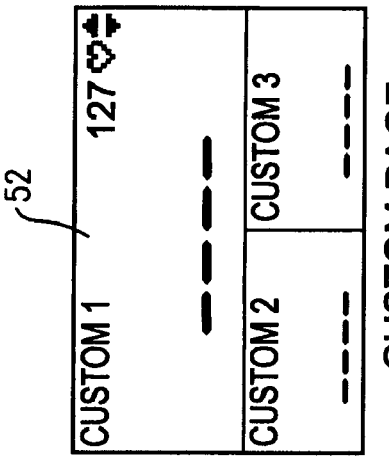
Fig. 8. CUSTOM PAGE
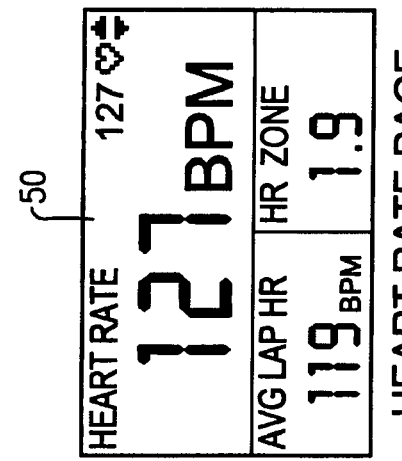
Fig. 7. HEART RATE PAGE

Fig. 9.

CALORIES PER MINUTE
10 TOTAL
| 60% FAT | 40% CARB |

PACE 19:00/mi
HEART RATE 60%

CALORIES PER MINUTE
14 TOTAL
| 50% FAT | 50% CARB |

PACE 13:00/mi
HEART RATE 70%

PACE 13:45/mile
DISTANCE 2.47 miles
HEART RATE 64%

CALORIES BURNED
175

FOOD EARNED
- LARGE APPLE
- SMALL CANDY BAR
- 1 SCOOP ICE CREAM

~60

NAVIGATION-ASSISTED FITNESS AND DIETING DEVICE

BACKGROUND OF THE INVENTION

1. Field of the Invention

The present invention relates to navigation devices. More particularly, the invention relates to a navigation-assisted fitness and dieting device which monitors a user's exercise and provides diet and fitness information which is geared toward persons trying to lose weight or improve their general fitness level.

2. Description of the Prior Art

The advent of the Atkins® diet, the South Beach® diet, and other popular diets and the heightened awareness of the importance of exercise has caused an increasing number of people to pay more attention to their diets and exercise regimens. Unfortunately, most people still lack a basic understanding of how their bodies react to different diets and exercise routines. For example, many people who wish to burn fat calories exercise at a high intensity level even though a higher percentage of fat calories are burned during lower intensity workouts.

Portable personal training devices have been developed to assist athletes and fitness buffs in monitoring and recording certain performance values while they train and exercise. One such device manufactured by Garmin International, Inc. of Olathe, Kans., can be worn on a user's wrist, includes a GPS receiver, and is operable to continuously monitor and track the user's heart rate, speed, distance traveled, pace, and calories burned and to provide directions or routes to a desired destination or along a desired route.

Although such training devices provide excellent information and performance features for athletes and serious fitness buffs, their features focus on athletic performance, speed/pace goals, and peak workout levels, rather than weight loss and general health. Similarly, these prior art training devices are not concerned with motivating users to exercise as athletes and serious fitness buffs need little motivation.

SUMMARY OF THE INVENTION

The present invention solves the above-described problems and provides a distinct advance in the art of dieting and fitness. More particularly, the invention relates to a navigation-assisted fitness and dieting device which monitors a user's exercise and provides diet and fitness information which is geared toward persons trying to lose weight or improve their general fitness level. The device also provides numerous features to motivate users to start and continue with exercise routines.

One embodiment of the present invention is a navigation-assisted fitness device broadly comprising a location determining component, a fitness monitoring component and a display. The location determining component determines location data for a user of the device as the user exercises. The fitness monitoring component is coupled with the location determining component and calculates fitness information for the user as the user exercises. The display displays the fitness information and other information and data.

The fitness information may include an indication of the intensity level of the user's exercise, the total amount of calories burned by the user during the exercise, the amount of fat calories burned, and the amount of carbohydrate calories burned. The device calculates the ratio of fat calories burned versus carbohydrate calories burned based on the exercise intensity level. As the user increases or decreases his or her exercise intensity level, the device recalculates and displays the ratio or percentage of total calories burned from fat reserves and from carbohydrate reserves.

The fitness information may also include an amount and type of exercise that must be completed to burn a target amount of calories. A user may indicate, for example, that he or she wants to burn one hundred calories. The fitness monitoring component then calculates that the user can run one mile, walk two miles, or bike three miles and then displays these options. The user may select one of the displayed exercise options and begin to complete this workout. While the user exercises according to the workout, the device monitors the user's exercise, estimates and displays the actual calories burned, and provides other useful health information.

The fitness information may also include an amount and type of certain food items that may be consumed by the user to equal the total calories burned during a workout. For example, the device may determine that the amount of calories burned during a workout equals the calories in an apple, a small serving of french fries, etc. and then display these food options.

The fitness information may also include estimated health improvements of the user as a result of one or more workouts. For example, the device may track and record performance information for the user over multiple workouts such as the total number of miles walked or run and then calculate and display an estimate of the user's improved circulation, heart rate, or body fat as a result of the workouts.

The fitness information may also include motivational information to encourage the user to start and continue with an exercise regime. For example, the device may track the total number of miles walked by a user over multiple workouts and then display the total miles over a map of the United States to show the user how far he or she has walked relative to points within the country. The device may also track the total number of calories burned by the user over multiple workouts and then equate this to the calories in certain quantities and types of food items and/or an estimated weight loss.

These and other important aspects of the present invention are described more fully in the detailed description below.

BRIEF DESCRIPTION OF THE DRAWING FIGURES

A preferred embodiment of the present invention is described in detail below with reference to the attached drawing figures, wherein:

FIG. 4 is a sample screen display or page of the fitness device.

FIG. 5 is another sample screen display or page of the fitness device.

FIG. 6 is another sample screen display or page of the fitness device.

FIG. 7 is another sample screen display or page of the fitness device.

FIG. 8 is another sample screen display or page of the fitness device.

FIG. 9 is another sample screen display or page of the fitness device.

FIG. 10 is another sample screen display or page of the fitness device.

FIG. 11 is another sample screen display or page of the fitness device.

Figure 1:
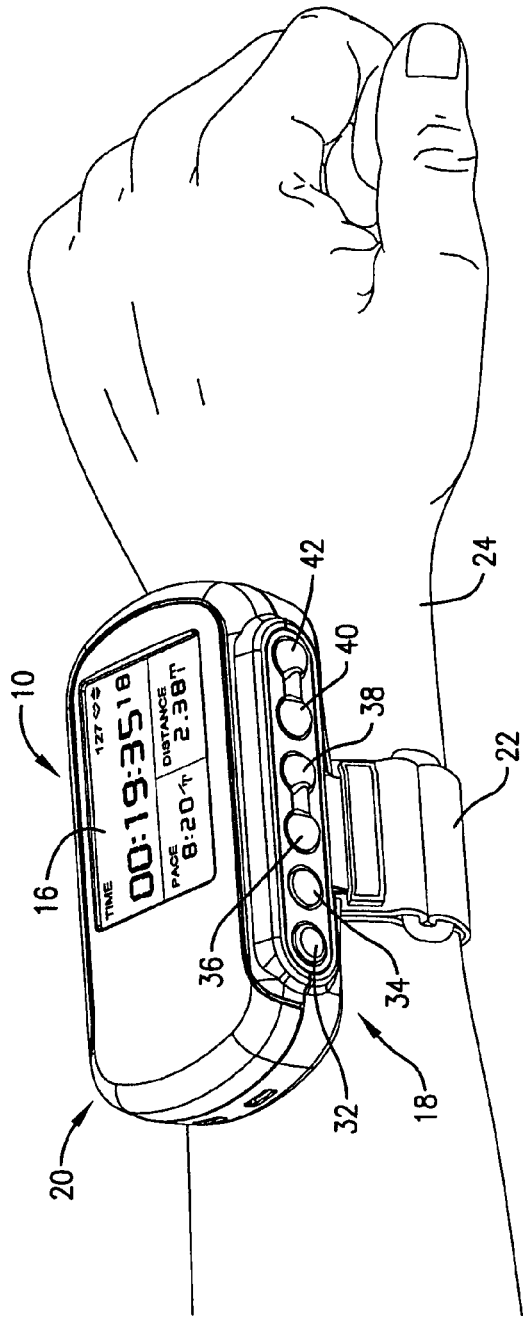
FIG. 1 is a perspective view of a navigation-assisted fitness and dieting device constructed in accordance with a preferred embodiment of the present invention and shown strapped to a user's wrist or forearm.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

The following detailed description of the invention references the accompanying drawings which illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 2:
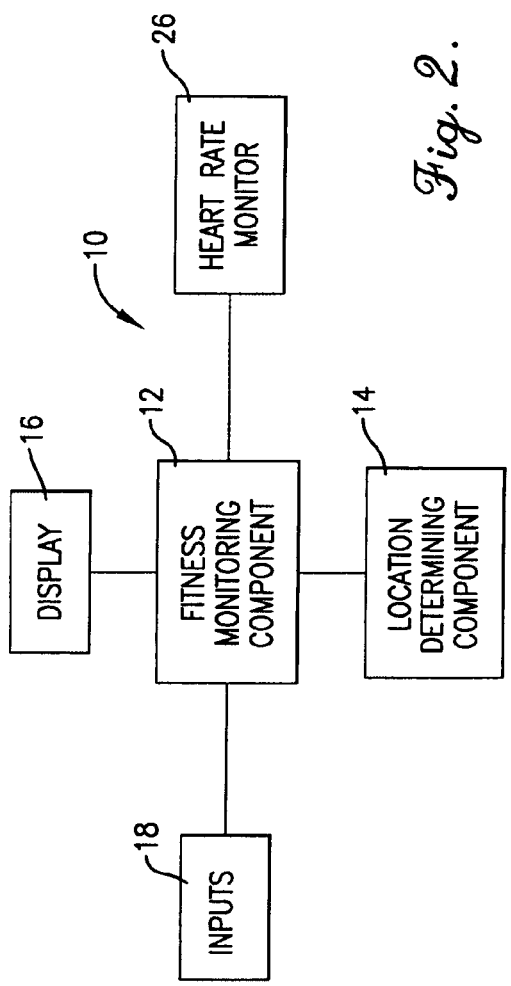
FIG. 2 is a block diagram depicting some of the components of the fitness device of FIG. 1.

Turning now to the drawing figures, and particularly FIGS. 1 and 2, a navigation-assisted fitness and dieting device 10 (also referred to as "fitness device" and "device" herein) constructed in accordance with a preferred embodiment of the invention is illustrated. The device 10 is especially suited for use by persons trying to lose weight and/or improve their general fitness level and is operable to continuously monitor and track a user's heart rate, distance traveled, pace, calories burned and other performance values while exercising, to provide fitness information that assists the user in meeting certain fitness and/or dieting goals, and to motivate the user to start and stick with an exercise regime.

The present invention can be implemented in hardware, software, firmware, or a combination thereof, but is preferably implemented with the components illustrated in FIGS. 1 and 2. Specifically, a preferred embodiment of the device 10 broadly comprises a fitness monitoring component 12; a location determining component 14; a display 16; one or more input devices 18; and an elongated housing 20 which encloses and protects the other components from moisture, vibration, and impact associated with the exercise or movement of the user. The device 10 may also include a strap 22 which removably secures the housing 20 to the user's forearm or wrist 24 and a heart rate monitor 26.

The fitness monitoring component 12 receives location information from the location determining component 14, monitors certain performance values of the user as the user exercises, calculates fitness information related to the user's exercise, and displays the fitness information on the display 16. The performance values may include, for example, the user's heart rate, speed or pace, cadence, and calories burned. The fitness information calculated by the device 10 may include the type and quantity of calories burned based on an intensity level of a workout; an amount and type of exercise that can be completed to burn a target amount of calories; an amount and type of food that may be eaten by the user as a reward for completing an exercise; the total calories burned, miles traveled, and/or duration of exercise as a result of a number of workouts or exercise sessions; and an estimate of the improvement in the user's health as a result of completion of workouts. Each of these types of fitness information is discussed in more detail below. Supplemental information may be entered into the fitness monitor component 12 from an external source as described below.

The fitness monitoring component 12 may consist of one or more processors, controllers, or other computing devices and preferably includes internal or external memory. The functions of the fitness monitoring component described herein may be performed by hardware, software, firmware or a combination thereof.

The location determining component 14 is preferably a global positioning system (GPS) receiver, and provides, in a substantially conventional manner, geographic location information for the device 10. The location determining component 14 may be, for example, a GPS receiver much like those provided in products by Garmin Corporation and disclosed in U.S. Pat. No. 6,434,485, which is incorporated herein by specific reference.

In general, the GPS is a satellite-based radio navigation system capable of determining continuous position, velocity, time, and direction information for an unlimited number of users. Formally known as NAVSTAR, the GPS incorporates a plurality of satellites which orbit the earth in extremely precise orbits. Based on these precise orbits, GPS satellites can relay their location to any number of receiving units.

The GPS system is implemented when a device specially equipped to receive GPS data begins scanning radio frequencies for GPS satellite signals. Upon receiving a radio signal from a GPS satellite, the device can determine the precise location of that satellite via one of different conventional methods. The device will continue scanning for signals until it has acquired at least three different satellite signals. Implementing geometrical triangulation, the receiver utilizes the three known positions to determine its own two-dimensional position relative to the satellites. Acquiring a fourth satellite signal will allow the receiving device to calculate its three-dimensional position by the same geometrical calculation. The positioning and velocity data can be updated in real time on a continuous basis by an unlimited number of users.

Although GPS enabled devices are often used to describe navigational devices, it will be appreciated that satellites need not be used to determine a geographic position of a receiving unit since any receiving device capable of receiving the location from at least three transmitting locations can perform basic triangulation calculations to determine the relative position of the receiving device with respect to the transmitting locations. For example, cellular towers or any customized transmitting radio frequency towers can be used instead of satellites. With such a configuration, any standard geometric triangulation algorithm can be used to determine the exact location of the receiving unit. In this way, personal hand held devices, cell phones, intelligent appliances, intelligent apparel, and others can be readily located geographically, if appropriately equipped to be a receiving unit.

Figure 3:
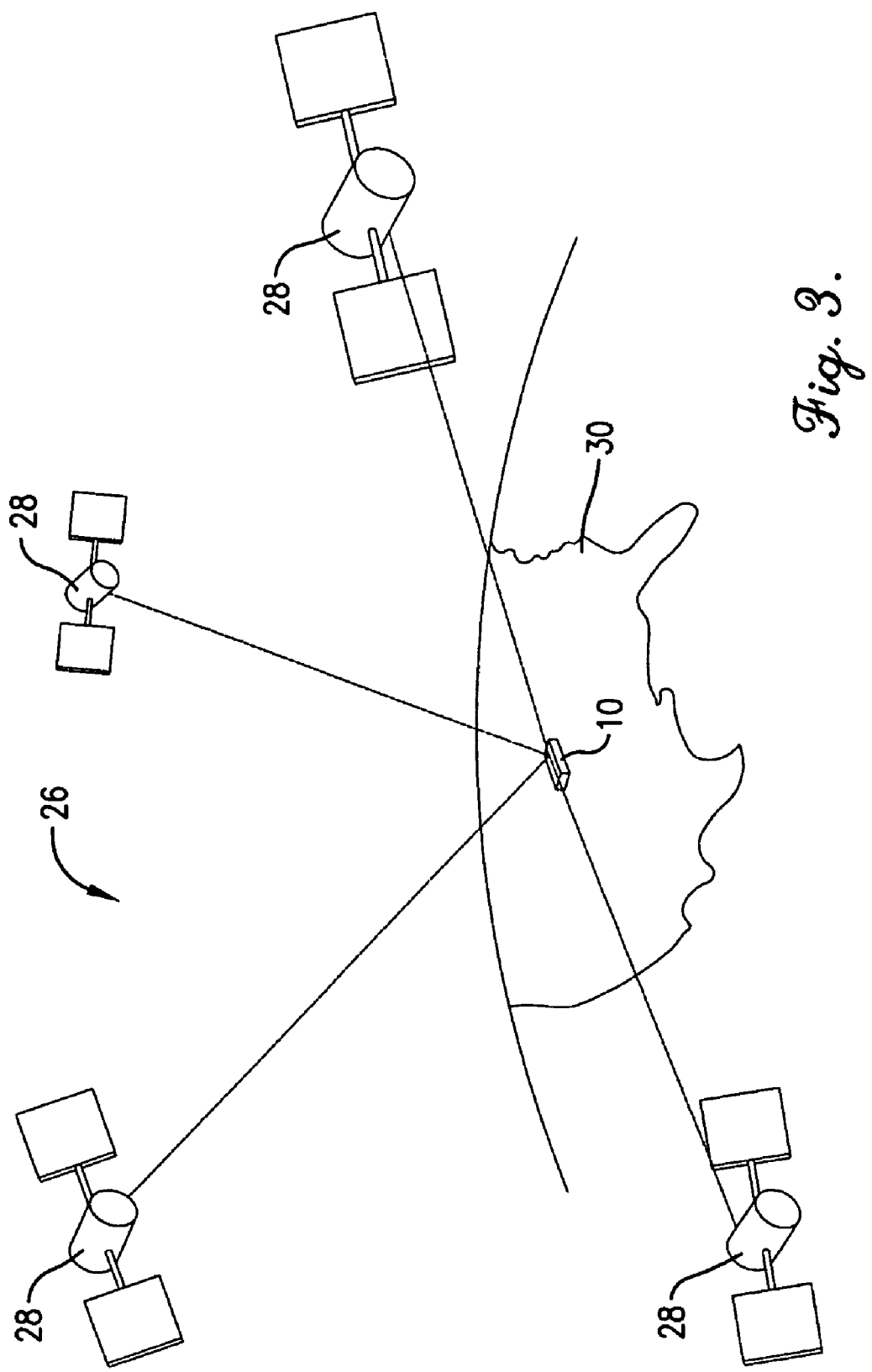
FIG. 3 is a schematic diagram of a Global Positioning System (GPS) that may be used to implement certain aspects of the present invention.

FIG. 3 shows one representative view of a GPS denoted generally by reference numeral 26. A plurality of satellites 28 are in orbit about the Earth 30. The orbit of each satellite 28 is not necessarily synchronous with the orbits of other satellites and, in fact, is likely asynchronous. A GPS receiver device 10 such as the ones described in connection with preferred embodiments of the present invention is shown receiving spread spectrum GPS satellite signals from the various satellites 28.

The spread spectrum signals continuously transmitted from each satellite 28 utilize a highly accurate frequency standard accomplished with an extremely accurate atomic clock. Each satellite 28, as part of its data signal transmission, transmits a data stream indicative of that particular satellite. The device 10 must acquire spread spectrum GPS satellite signals from at least three satellites for the GPS receiver device to calculate its two-dimensional position by triangulation. Acquisition of an additional signal, resulting in signals from a total of four satellites, permits the device 10 to calculate its three-dimensional position.

The location determining component 14 may include one or more processors, controllers, or other computing devices and memory for storing information accessed and/or generated by the processors or other computing devices. The location determining component 14 is operable to receive navigational signals from the GPS satellites 28 to calculate a position of the device 10 as a function of the signals. The location determining component 14 is also operable to calculate a route to a desired location, provide instructions to navigate to the desired location, display maps and other information on the display screen 16, and to execute other functions described herein. The memory may store cartographic data and routing used by or generated by the location determining component's computing devices. The memory may be integral with the location determining component 14, stand-alone memory, or a combination of both. The memory may include, for example, removable TransFlash cards.

The location determining component 14 also includes an antenna, which is preferably positioned within the housing 20 opposite the display 16, to assist the location determining component in receiving signals. The antenna is preferably a GPS patch antenna or helical antenna but may be any other type of antenna that can be used with navigational devices. The antenna may be mounted directly on or in the housing or may be mounted external to the housing. The antenna is preferably protected from adverse conditions, such as those described above, by being entirely enclosed within the housing. Additionally, any harmful physical contact that can occur from a user's accidental contact with a conventional, pointed, antenna is eliminated as the antenna has no sharp points protruding from the housing. Furthermore, the placement of the antenna adjacent to the display provides the antenna with adequate reception, regardless of the user's physical alignment, as the antenna is always orientated away from the user. Alternatively, the antenna may be operable to broadcast signals and may be positioned elsewhere within the housing or external to the housing.

The display screen 16 is coupled with the fitness monitoring component 12 and the location determining component 14 for displaying fitness and location data and information. The display screen 16 is preferably an LCD display capable of displaying both text and graphical information. The display 16 may also be backlit such that it may be viewed in the dark or other low-light environments. One example of a display that may be used with the present invention is a 100×64 pixel display with a bright white LED backlight. As illustrated in FIG. 1, the display screen 16 is preferably positioned on a front face of the housing for easy viewing.

The inputs 18 are preferably positioned on the side of the housing such that they may be easily accessed by the user during exercise. The inputs 18 may include descriptive markings that identify their function. Preferably, the inputs 18 are positioned such that the user may operate them with one hand, thus enabling the user to continue exercising while operating the device. The inputs may be buttons, switches, keys, an electronic touchscreen associated with the display, voice recognition circuitry, or any other elements capable of controlling the performance monitoring component and location determining component.

In one embodiment, the inputs 18 may comprise a Power input button 32 which turns the device on and off and which enables the back-light; a Mode input 34 to change between operating modes of the fitness monitoring component 12 and the location determining component 14; a Reset/Lap input 36 to reset a timing function; an Enter or Start/Stop input 38 to start and stop the timing function or to confirm a menu selection; and a Down Arrow input 40 and an Up Arrow input 42 to choose a data screen or change selections within a data screen. Alternatively, the inputs 18 may include other combinations of inputs which effectively operate the device.

The device 10 may also include a speaker for providing audible instructions and feedback, a microphone for receiving voice commands, an infrared port for wirelessly receiving and transmitting data and other information from and to nearby electronics, and other information, and even a cellular or other radio transceiver for wirelessly receiving and transmitting data from and to remote devices. For example, the radio transceiver may permit the device 10 to communicate with a remote server such as the one shown in FIG. 14 and described below.

Figure 14:
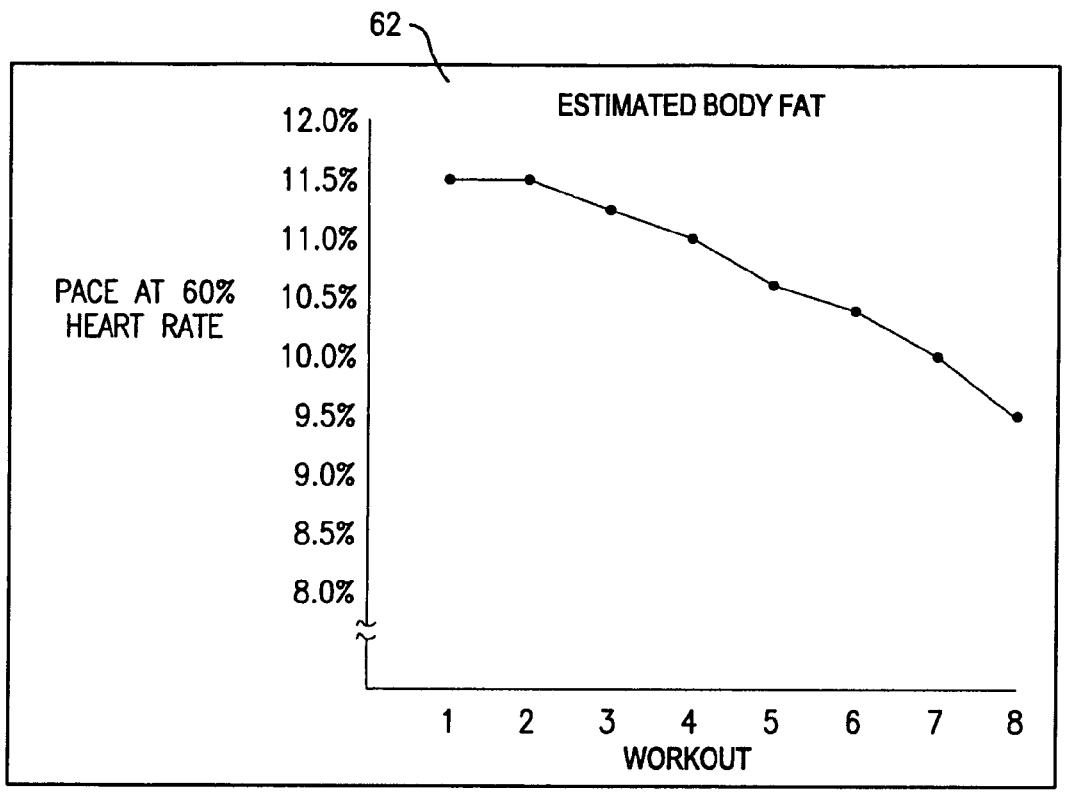
FIG. 14 is another sample screen display or page of the fitness device.

The device 10 may also include a number of I/O ports that permit data and other information to be transferred to and from the fitness monitoring component 12 and the location determining component 14. The I/O ports may include a TransFlash card slot for receiving removable TransFlash cards and a USB port for coupling with a USB cable connected to another computing device such as a personal computer as depicted in FIG. 14. Navigational software, cartographic maps and other data and information may be loaded in the navigational device via the I/O ports, the wireless transceivers, or the infrared port mentioned above.

The components shown in FIG. 2 and described above need not be physically connected to one another since wireless communication among the various depicted components is permissible and intended to fall within the scope of the present invention.

The housing 20 is preferably constructed from a suitable lightweight and impact-resistant material such as, for example, plastic, nylon, aluminum, or any combination thereof. The housing 20 preferably includes one or more appropriate gaskets or seals to make it substantially waterproof or resistant. The housing 20 may include a location for a battery, or other power source, associated with the device 10. Though shown as being substantially elongated, the housing 20 may take any suitable shape or size, including, for example, ergonomic shapes molded to substantially correspond to a portion of the user's forearm whereupon or against which the housing 20 is meant to rest. Preferably, the housing has a width between one and six inches, a height between one-half of an inch and six inches, and a depth between one-sixteenth of an inch and three inches. However, the particular size, weight and configuration of the housing may be changed without departing from the scope of the present invention.

The elongated shape of the housing 20 allows the device 10 to be securely supported by the user's forearm or wrist such that the device 10 remains securely attached to the user, even during exercise or other periods of activity. The shape and dimensions of the housing 20 also allow the user to operate the device 10 with one hand, as the housing 20 may be gripped by the user's fingers while inputs described below are operated by the user's thumb. Additionally, the housing 20 has a large surface area to contain the components shown in FIG. 2 and a generally flat, rounded, profile to reduce harmful contact of the device 10 to the user or an external element.

The strap 22 is preferably made of lightweight and resilient fabric, such that the strap may encircle the user's arm without discomfort while still adequately securing the housing 20 to the user's forearm. The strap 22 is removably secured to the housing 20 by the attachment of securing elements to connecting elements. The connecting elements and securing elements may be any conventional reciprocal connecting and securing pair, such as a hooks, latches, clamps, snaps, buttons, etc. The strap 22 is attached to the user's forearm by encircling the strap around the user's forearm and securing the strap 22 to itself through the use of hooks, latches, clamps, or other conventional fastening elements. Alternatively, the strap 22 may be configured to attach to other parts of the user, such as the user's leg, waist, wrist, or upper arm.

A user may operate the device 10 by manipulating the inputs 18. For example, after turning the device on with the Power button 32, the user may press the Mode input 34 to switch between a Timer mode depicted in FIG. 4 and a Menu mode depicted in FIG. 5. The Timer mode initially displays a Time and Speed page 44 (sometimes referred to as a Speed page or a Timer page). The menu mode displays a Main Menu page 46. From the initial Timer page 44, the user may operate the Up and Down arrow buttons 40,42 to access data pages including a Lap page 48 depicted in FIG. 6, a Heart Rate page 50 depicted in FIG. 7, and a custom page 52 depicted in FIG. 8.

By depressing the Mode button 34, a user may also enable navigation capabilities of the location determining component 14. The navigation capabilities may allow a user to display the user's current geographic location on the display 16, map the user's location on the display 16, chart a desired course of travel on the display, or find a desired location on a map generated on the display. Additional navigation capabilities, such as conventional functions found in known navigation units, may also be provided by the location determining component. Supplemental navigational information, such as additional maps or geographical information, may be entered into the location determining component from an external source, such as the computer shown in FIG. 14.

The heart rate monitor 26 preferably includes a pair of heart rate sensors carried on a strap designed to be worn below the user's breastplate. The sensors are connected to a transmitter which wirelessly transmits heart rate data to the performance monitoring component. When the user puts on the heart rate monitor, it begins transmitting heart rate data plus a unique, randomly-selected code. When the device is turned on, it begins "listening" for data from the heart rate monitor. Once the device "hears" two or more transmissions of heart rate data that contain the same unique code, it pairs with the heart rate monitor, creating a unique wireless link.

Once paired, the device 10 will never receive conflicting signals from another heart rate monitor, so the user can exercise in close proximity to other heart rate monitors without fear of interference. If the device loses a heart rate signal, the pairing process begins again automatically.

The user follows these steps to successfully pair the device 10 with his or her heart rate monitor 26: 1) position the heart rate monitor 26 and establish a strong connection between it and the user's pulse; 2) position the device 10 within range of the heart rate monitor 26 (90-110 cm or 35-43 inches); and 3) stand at least six feet away from any other heart rate monitor (only while pairing).

The device 10 may permit the user to select an exercise from a plurality of different types of exercise and display information specific to the selected exercise. For example, the device 10 may permit the user to select walking, running or other. "Other" can be used for nearly any sport or exercise. Other embodiments of the device could permit selection of different and additional exercises or workouts without departing from the scope of the present invention.

Once a workout or exercise is selected, the fitness monitoring component 12 displays data pages with calculated units which are specific to the selected exercise, and may calculate performance values such as calories burned and maximum heart rate for the exercise. For example, if the user selects walking, the Timer mode page 44 depicted in FIG. 4 shows a "pace" (rather than "speed") in units of min/mile or min/km. The device 10 may also organize workout data by type of exercise and store workout data for all exercises. The device 10 also displays the details of a workout differently depending on the exercise selected, by, for example, changing the pace units as discussed above. The device 10 may also display sports specific icons, such as a graphical image of a person running for the Running mode and a graphical image of a person walking for the walking mode.

The device 10 may also offer other training features that allow a user to set goals and alerts, train with a Virtual Partner, and program interval workouts. For example, the device 10 may provide audible and/or visual alerts when the user reaches certain time, distance, pace, speed, cadence or heart rate goals. A Virtual Partner mode allows the user to enter the distance, time or pace/speed at which he or she wishes to complete a workout. Workouts can also be created externally, such as with a Training Center software provided by Garmin International, and then transferred to the device.

In accordance with one important aspect of the present invention, the device 10 also calculates and displays fitness information which is geared toward persons trying to lose weight or improve their general fitness level. The device 10 also provides numerous features to motivate users to start and continue with an exercise routine and thus serves as a "virtual coach".

In one embodiment, the fitness information includes an indication of the intensity level of the user's exercise, the total amount of calories burned by the user during the exercise, the amount of fat calories burned, and the amount of carbohydrate calories burned. This information is very valuable to persons trying to lose weight because most people lack an understanding of how different forms and intensities of workouts affect weight loss. For instance, some people assume that the intensity of exercise must be kept very high to burn fat as a fuel and some people assume the opposite. In truth, at low exercise intensities, a high percentage of the total energy expenditure during exercise is derived from fat. Thus, as the exercise intensity increases, the percentage of fat used as fuel decreases. However, the total rate (not relative percentage) of fat oxidation during exercise is typically greatest at higher exercise intensities that are below the lactate threshold. Thus, the regulation of fuel selection during exercise is under complex control and is dependent upon several factors, including diet and the intensity and duration of exercise. In general, carbohydrates are used as the major fuel source during high-intensity exercise. During prolonged exercise, there is a gradual shift from carbohydrate metabolism toward fat metabolism. Proteins contribute less than 2% of the fuel used during exercise of less than one hour's duration. During prolonged exercise (i.e., three to five hours' duration), the total contribution of protein to the fuel supply may reach 5%-15% during the final minutes of prolonged work.

The fitness monitoring component 12 is programmed to take these factors into account when calculating the amount of fat calories burned versus carbohydrate calories burned during a workout. The device 10 then displays this information so the user can quickly and easily graphically see his or her exercise results and adjust exercise intensity to achieve a particular calorie-burning objective. As the user increases or decreases the intensity level of an exercise, the device recalculates and displays new values for total calories burned, fat calories burned and carbohydrate calories burned.

For example, FIG. 9 shows an exemplary screen display 54 for when the user is walking at a pace of 19:00/mile and has a heart rate of 60%. At this pace and intensity level, the user is burning 10 calories per minute, 60% of which are from fat and 40% of which are from carbohydrates. FIG. 10 shows a display 56 illustrating that when the user increases his or her pace to 13:00/mile and heart rate to 70%, he or she is burning 14 calories per minute, 50% of which are from fat and 50% of which are from carbohydrates. The device 10 therefore provides highly useful health information that allows the user to tailor the intensity of a workout to meet certain weight loss or control goals. The particular calorie numbers described and illustrated herein are for illustrative purposes only and aren't necessarily from an actual person's workout.

The fitness information may also include an amount and type of exercise that must be completed to burn a target amount of calories. A user may operate the inputs 18 to indicate, for example, that he or she wants to burn 200 calories as depicted by the display in FIG. 12. The fitness monitoring component 12 may then present several exercise options for reaching this goal. After the user selects one of the displayed exercise options, the device calculates and displays the distance and/or duration of the selected exercise that must be performed to burn the target amount of calories. While the user performs the exercise, the device monitors the user's performance by tracking the actual distance traveled, pace, etc.

The fitness information may also include an amount and type of certain food items that may be consumed by the user to equal the total calories burned during a workout as depicted by the display 60 in FIG. 11. For example, the device 10 may determine that the amount of calories burned during a workout equals the calories in an apple, a small candy bar, a scoop of ice cream, and then display these food options.

Figure 15:
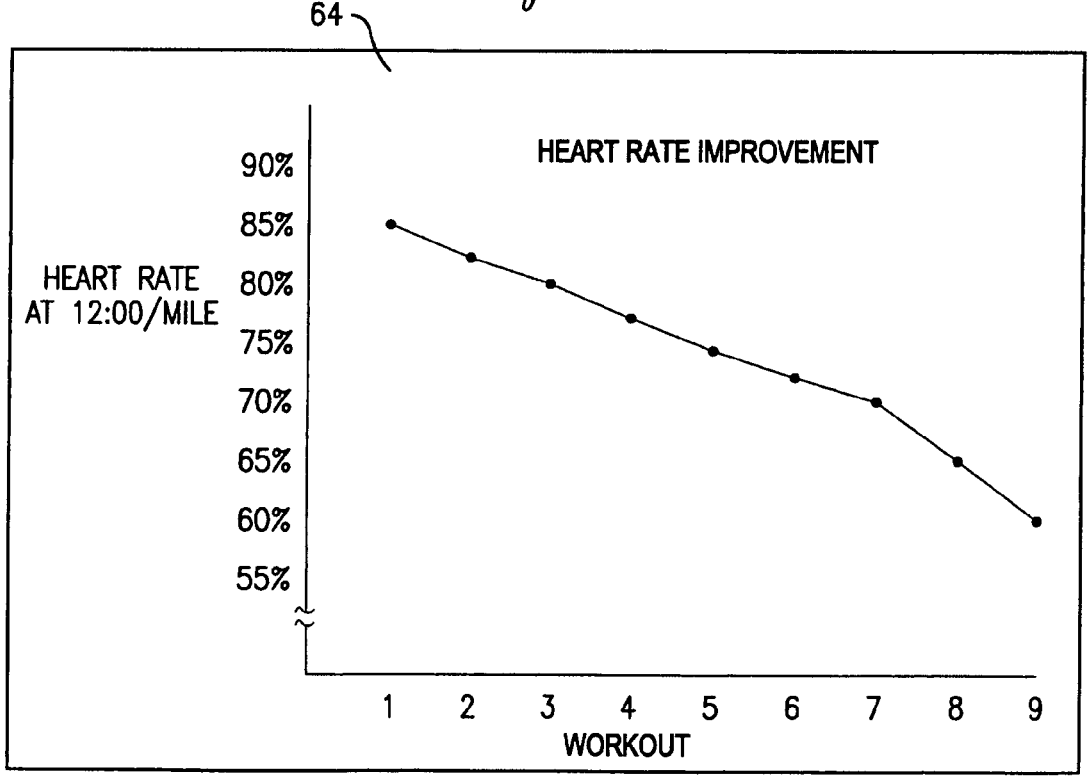
FIG. 15 is another sample screen display or page of the fitness device.
Figure 16:
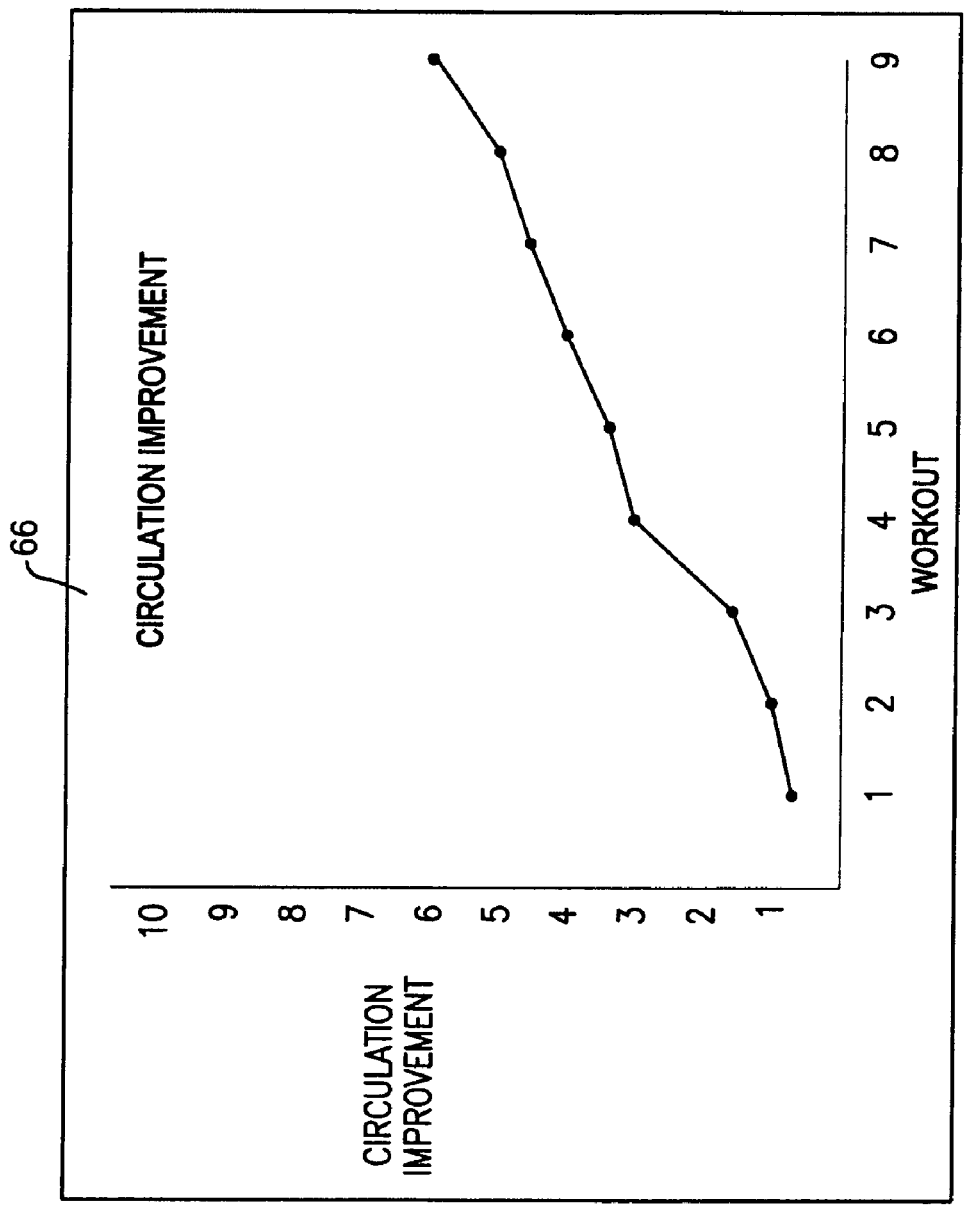
FIG. 16 is another sample screen display or page of the fitness device.

The fitness information may also include estimated health improvements for the user as a result of one or more workouts. For example, the device may track and record performance information for the user over multiple workouts such as the total number of miles walked or run and then calculate and display an estimate of the user's improved body fat as depicted by the display 62 in FIG. 14, heart rate as depicted by the display 64 in FIG. 15, and circulation as depicted by the display 66 in FIG. 16. To provide more accurate health improvement estimates, the device may permit the entry of information used to calculate these values. For example, a user could enter his or her weight before and after completion of a number of workouts to be used to more accurately estimate the user's improved body fat percentage.

Figures 12, 13:
FIG. 12 is another sample screen display or page of the fitness device.
FIG. 13 is another sample screen display or page of the fitness device.

The fitness information may also include motivational information to encourage the user to start and continue with an exercise regime. For example, the device may track the total number of miles walked by a user over multiple workouts and then display an indication 68 of the total miles over a map of the United States as depicted by the display 70 in FIG. 13 to show the user how far he or she has walked relative to points within the country. The device may also track total miles, then provide a text or audio message such as "You have now walked across Texas" when the user has walked this many total miles. The device may also track the total number of calories burned by the user over multiple workouts and then equate this to the calories in certain quantities and types of food items also as depicted in FIG. 13.

The device 10 may also be programmed to automatically adjust performance goals if a user misses or shortens any workouts. For example, if a user starts an exercise routine in which the user walks three miles per day and increases his or her pace by 5% per workout, but the user then misses four workouts, the device may automatically lower the pace goals so the user doesn't become discouraged.

The device may also include an alarm and calendar features to keep track of scheduled workouts and to alert the user before a workout.

Figure 17:
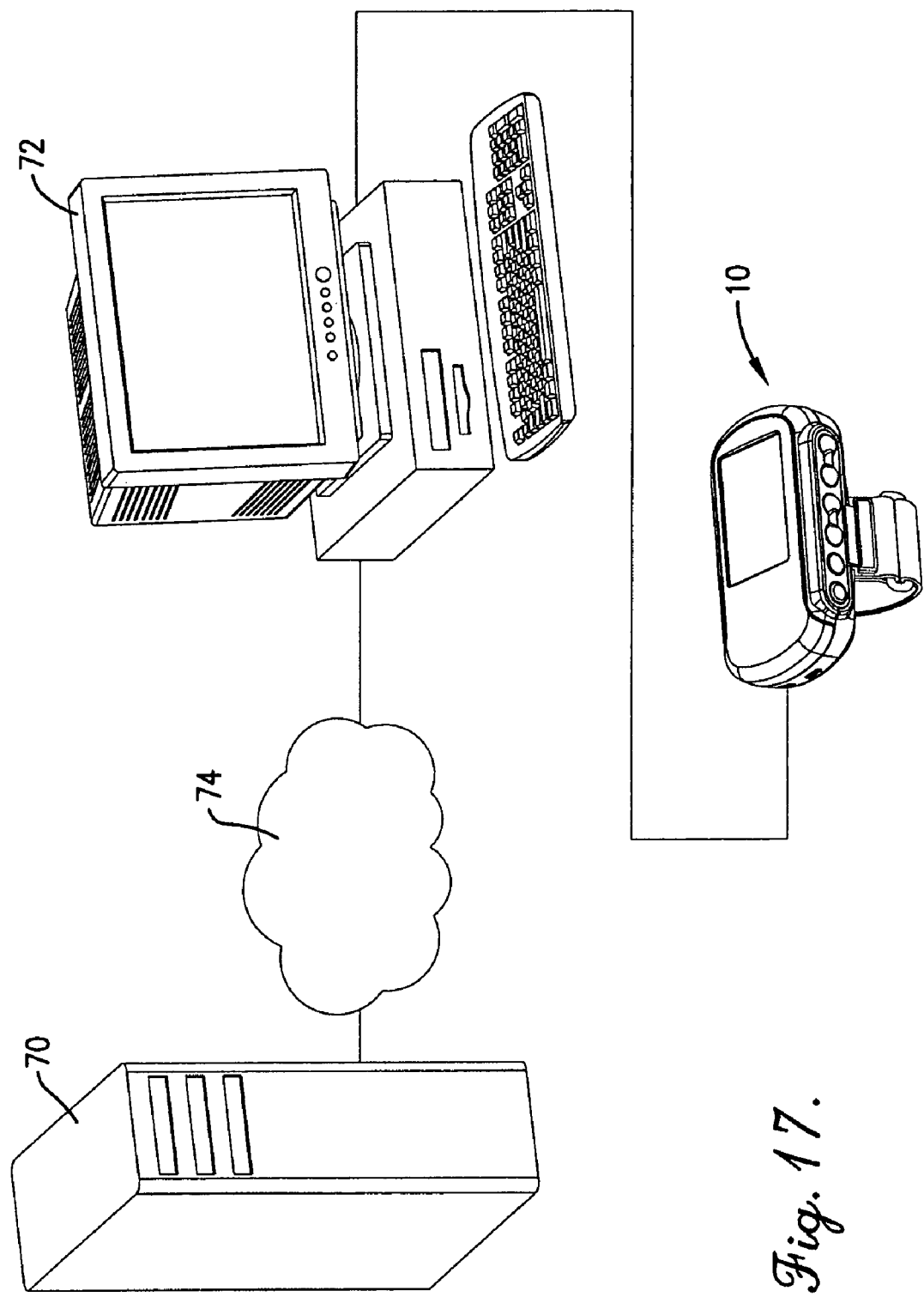
FIG. 17 is a schematic diagram of computer equipment shown coupled to the fitness device of FIG. 1 for the purpose of downloading data to the device.

Information and data may be downloaded to the device from a server 70 via a user computer 72 coupled to the server through a communications network 74 as depicted in FIG. 17. The communications network 74 may be the Internet, a local area network, a wireless communication network, or any other conventional network. Once downloaded, the data can then be transferred from the computer 72 to the device 10 via a wired or wireless link such as an infrared link, Bluetooth connection, or USB connection.

Alternatively, the information and data can be directly transferred from the server 70 to the device 10 via a wired or wireless data link. For example, the device 10 may be equipped with a cellular transceiver or other wireless data link for communicating directly with the server or other external computer. Data and information may also be transferred directly to the device 10 from a similar device.

The device 10 may also include an entertainment component operable to execute at least one game that is stored in memory or otherwise accessible by the entertainment component. Preferably, the entertainment component is operable to execute a plurality of games. In operation, a user manipulates a plurality of inputs to select a particular game, which is displayed on a display, and participate in the game. The entertainment component may connect with other similar entertainment components, by a connection formed through a contact, antenna, or other connection elements, to allow the user to interact with multiple persons during the course of the game. The game may interface with the user's geographic location information, such as the user's current geographic location, to provide a real-world link in an executed game. Games or additional entertainment information may be entered into the entertainment component from an external source, such as a computer or computer network. Other features and aspects that may be included in the present invention are described in U.S. Pat. Nos. 6,837,827; 6,853,955; and patent application Ser. No. 10/786,377, entitled WEARABLE GPS DEVICE and filed on Feb. 25, 2004, all of which are incorporated by reference into the present application.

Although the invention has been described with reference to the preferred embodiment illustrated in the attached drawing figures, it is noted that equivalents may be employed and substitutions made herein without departing from the scope of the invention as recited in the claims. For example, some of the components of the device 10 can also be embodied as computer hardware circuitry or as a computer-readable program, or a combination of both. More specifically, the programs can be structured in an object-orientation using an object-oriented language such as Java, Smalltalk, C++, and others, and the programs can be structured in a procedural-orientation using a procedural language such as C, PASCAL, and others. The software components communicate in any of a number of means that are well-known to those skilled in the art, such as application program interfaces (A.P.I.) or interprocess communication techniques such as remote procedure call (R.P.C.), common object request broker architecture (CORBA), Component Object Model (COM), Distributed Component Object Model (DCOM), Distributed System Object Model (DSOM) and Remote Method Invocation (RMI). Any programming methodology, programming language, programming interface, operating system, or computing environment, now known or hereafter developed, can be readily deployed, without departing from the tenets of the present invention and all such implementation specific embodiments are intended to fall within the broad scope of the present invention.

Having thus described the preferred embodiment of the invention, what is claimed as new and desired to be protected by Letters Patent includes the following:

1. A navigation-assisted fitness device comprising:
    a GPS receiver for receiving satellite signals from a plurality of GPS satellites and for calculating current location data for a user as the user exercises;
    a fitness monitoring component coupled with the GPS receiver for calculating fitness information for the user as the user exercises, the fitness information including an intensity level of the exercise and an indication of an amount of fat calories and carbohydrate calories being burned as a result of the intensity level;
    a display for displaying the fitness information in real-time, the displayed fitness information including a separate indication of the amount of fat calories and carbohydrate calories being burned;
    a portable housing for housing the GPS receiver, the fitness monitoring component, and the display; and
    a strap for removably attaching the housing to the user's wrist or forearm.

2. The fitness device of claim 1, wherein the fitness information further includes a total amount of calories burned by the user during the exercise.

3. The fitness device of claim 1, wherein the intensity level is an indication of the user's heart rate while performing the exercise.

4. The fitness device of claim 1, wherein the fitness monitoring component is operable to receive from the user an indication of a target amount of calories to burn and to determine an amount and type of exercise that can be completed to burn the target amount of calories.

5. The fitness device of claim 4, wherein the fitness monitoring component is operable to determine several exercise options for the amount and type of exercise that must be completed to burn the target amount of calories.

6. The fitness device of claim 1, wherein the fitness information includes an indication of a type and amount of food that may be consumed by the user to equal the total calories burned during the exercise.

7. The fitness device of claim 1, further including a heart rate monitor coupled with the fitness monitoring component for monitoring a heart rate of the user and for sending corresponding heart rate data to the fitness monitoring component.

8. The fitness device of claim 1, wherein the location data includes geographic coordinates.

9. The fitness device of claim 1, wherein the location data is displayed over a cartographic map.

10. The fitness device of claim 1, wherein the fitness monitoring component is operable to track and record a total distance traveled by the user over multiple exercise sessions and to display a representation of the total distance over a map.

11. The fitness device of claim 1, wherein the fitness monitoring component is operable to track and record a total amount of calories burned by the user over multiple exercise sessions and to display an indication of a type and amount of food that is equivalent to the total calories burned.

12. The fitness device of claim 1, wherein the fitness monitoring component is further operable to present a real-time comparison of the amount of fat calories being burned to the amount of carbohydrate calories being burned.

13. The fitness device of claim 12, wherein the fitness monitoring component is operable to generate a ratio of burned fat calories to burned carbohydrate calories.

* * * * *